US00PP29927P3

(12) United States Plant Patent
Austin

(10) Patent No.: US PP29,927 P3
(45) Date of Patent: Dec. 4, 2018

(54) ***ROSA HYBRIDA* SHRUB NAMED 'AUSOWLISH'**

(50) Latin Name: *Rosa hybrida*
Varietal Denomination: AUSowlish

(71) Applicant: David Austin Roses Ltd., Albrighton, Wolverhampton (GB)

(72) Inventor: David J. C. Austin, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 15/731,138

(22) Filed: Apr. 24, 2017

(65) Prior Publication Data

US 2018/0092265 P1 Mar. 29, 2018

(30) Foreign Application Priority Data

Sep. 28, 2016 (GB) ..... 5/2133
Sep. 29, 2016 (EP) ..... 2016/2362

(51) Int. Cl.
*A01H 5/02* (2018.01)
*A01H 6/74* (2018.01)

(52) U.S. Cl.
USPC ..... Plt./106
CPC ..... *A01H 5/02* (2013.01); *A01H 5/0222* (2013.01); *A01H 6/749* (2018.05)

(58) Field of Classification Search
USPC ..... Plt./106
See application file for complete search history.

*Primary Examiner* — Anne Marie Grunberg
(74) *Attorney, Agent, or Firm* — KPPB LLP

(57) ABSTRACT

A variety of rose plant of the shrub class, named 'AUSowlish'. The 'AUSowlish' is a variety of a rose with blooms that are robust to inclement weather. The flowers are of a peach color, with young buds that are yellow flushed with a soft orange-red, and cupped rosette blooms that have a medium strength tea fragrance. The plant matures into a rounded, bushy shrub with a mid-green foliage and few thorns.

1 Drawing Sheet

Classification: The present invention relates to a new *Rosa hybrida* shrub of the market class 'English Rose'.

Variety denomination: The new plant has the varietal denomination 'AUSowlish'.

CROSS-REFERENCE TO RELATED APPLICATION

The present application claims priority to European CPVO 2016/2362, filed Sep. 29, 2016, and United Kingdom Application No. 5/2133, filed Sep. 28, 2016, the disclosures of which are herein incorporated by reference in their entirety.

ORIGIN OF INVENTION

This invention relates to a new and distinct variety of shrub rose plant named 'AUSowlish', which was originated from the cross-pollination of the two 'unnamed' and unpatented seedlings of *Rosa hybrida*.

BACKGROUND OF THE INVENTION

The primary objective of this breeding was to produce a rose variety with flowers of peach coloring, with young buds that are yellow flushed with a soft orange-red, and that form medium-sized, cupped rosette blooms which are robust and stand up to inclement weather when fully opened, and that have a medium strength tea fragrance.

SUMMARY OF THE INVENTION

Among the features which distinguish the new variety from others presently available and commercial rose cultivars known to the inventor is the following combination of characteristics: peach colored blossoms, with buds that show some yellow with orange-red sepals as they begin to open; robust cupped rosette blooms; mid-green foliage; few thorns; and a medium-strength tea fragrance.

Asexual reproduction of the new variety by budding as performed at Bowling Green Lane in Albrighton, Britain shows that the foregoing and other distinguishing characteristics come true to form and are established and transmitted through succeeding asexual propagations. 'AUSowlish' may be asexually propagated by budding. The budding successfully occurred on the plant/rootstock *Rosa dumetorum* 'Laxa' for the observed plants.

COMPARISON WITH PARENTS

The maternal and paternal parents of 'AUSowlish' are two unnamed seedlings. The new rose may be distinguished from its maternal parent, by the following combination of characteristics: the maternal parent has a more orange coloring, fewer petals and a more lax growth. The new rose may be distinguished from its pollen parent, by the following combination of characteristics: the paternal parent has a more yellow color with fewer petals and a more upright growth.

COMPARISON WITH THE CLOSEST COMMERCIALLY AVAILABLE CULTIVAR

The closest commercially available cultivars to the new variety are the 'AUSnyson' (U.S. Plant Pat. No. 22,171) and 'AUSjo' (unpatented). The new rose may be distinguished from the 'AUSnyson' and 'AUSjo' roses based on the color of their buds, while 'AUSowlish' has a bud color that is a combination of RHS 2D (yellow group) and RHS 35B (orange red), 'AUSnyson' has a bud color of RHS 53A (red group) and 'AUSjo' has a bud color of RHS 20A (yellow orange). Further, when the flower is open the color of the 'AUSowlish' bloom is RHS 10D (yellow group) compared with RHS 34C (orange-red) for 'AUSnyson' and RHS 13C (yellow group) for 'AUSjo'. Finally, both 'AUSnyson' and 'AUSjo' have many prickles, whereas 'AUSowlish' has few prickles.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (2001) except where common terms of color definition are employed.

DESCRIPTION OF THE NEW VARIETY

Observations of budded 'AUSowlish' specimens were made at the nursery at David Austin Roses Limited in Albrighton, Wolverhampton, United Kingdom. The following description is of 2 year-old rose plants of the new variety grown in a garden environment in Albrighton, Britain in the month of June. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

- *Size*.—About 1.9 cm long and 1.6 cm in diameter when the petals start to unfurl.
- *Form*.—The bud form is pointed globular.
- *Color*.—When sepals first divide, the bud color is RHS 1C (green yellow group) and RHS 35B (orange-red group). When half blown, the upper sides of the petals are RHS 2D (yellow group), and the lower sides of the petals RHS 2D (yellow group).
- *Calyx*.—Shape: opens to a star shape, with the sepals finally folding back against the stems. Length: 7.0 cm. Diameter: 7.0 cm.
- *Sepals*.—Arrangement: Regularly arranged. Color: Upper Surface: RHS 145B (yellow-green group). Lower Surface: RHS 143C (green group) plus N34C (orange-red group). Length: 24 mm. Width: 9 mm. Shape: Lanceolate. Surface texture: Upper Surface: Downy. Lower Surface: Smooth. Number: There are 3 lightly appendaged sepals, and 2 unappendaged sepals with hairy edges.
- *Receptacles*.—Color: RHS 143B (green group). Shape: Apple. Size: Medium, about 1 cm long×0.9 cm wide. Surface: Smooth.
- *Peduncle*.—Length: Short, averaging about 9 cm. Surface: Glandular. Color: RHS 143B (green group). Strength: Normal.

Blooms:

- *Size*.—Medium, average open diameter is about 6.5 cm.
- *Borne*.—Several together having a rounded shape.
- *Stems*.—Strength: Normal, average length is about 15 cm. Diameter: 5 mm.
- *Form*.—When first open, bloom is cupped. Permanence of bloom: outer petals curl back.

Petalage: Number of petals under normal conditions: 55.

- *Color*.—The upper sides of the petals are RHS 10D (yellow group). The reverse sides of the petals are RHS 10D (yellow group). The base of the petals has a yellow spot that is RHS 12A (yellow group).
- *Variegations*.—None.
- *Discoloration*.—The general tonality at the end of the first day is RHS 10D (yellow group), and at the end of the third day is RHS N10D (yellow group).
- *Fragrance*.—Moderate. Character of fragrance: Tea.

Petals:

- *Texture*.—Smooth.
- *Size*.—Width: 25 mm. Length: 35 mm.
- *Surface*.—Smooth.
- *Shape*.—Obovate.
- *Margin*.—Heavily notched.
- *Apex shape*.—Rounded, although notched with some large incisions.
- *Base shape*.—Acute.
- *Form*.—Incurved.
- *Arrangement*.—Irregular.
- *Petaloids*.—Number: Around 15-20. Color: RHS 10D (yellow group). Length: up to 25 mm. Width: up to 10 mm. Shape: Narrow obovate. Margin: Irregular.
- *Persistence*.—Petals drop off cleanly before drying.
- *Lastingness*.—On the plant: fair, about 4-5 days. As a cut flower: not tested.

Reproductive parts:

- *Stamens*.—Number: 60. Length: 1 cm.
- *Anthers*.—Length: 3 mm. Color: RHS 14C (yellow-orange group). Arrangement: Regular around styles with some mixed with petaloids.
- *Filaments*.—Color: RHS 14B (yellow-orange group). Length: 7 mm.
- *Pollen*.—Color: RHS 14A (yellow-orange group). Amount: Abundant.
- *Pistils*.—Number: 25. Length: 2 mm.
- *Styles*.—Color: RHS 151C (yellow-green group). Length: 1.5 mm.
- *Stigmas*.—Color: RHS 151C (yellow-green group). Length: 0.5 mm.
- *Hips*.—NONE Observed.

PLANT CHARACTERISTICS

Plant form: Shrub.

Plant growth: Medium.

Age to maturity: 1 years.

Mature plant: Height: 1 m 20 cm. Width: 90 cm.

Rootstock: 'Dr. Huey' in the U.S. and *Rosa dumetorum* 'Laxa' for the observed plants in the UK.

Foliage:

- *Number*.—Leaflets on normal mid-stem leaves is: 5 mostly (including terminal leaflet).
- *Size*.—Medium, about 13.5 cm long×11 cm wide.

*Quantity*.—Normal. Number of leaves per flowering stem is: 10.

*Color*.—New foliage: Upper side: RHS 152B (yellow-green group). Lower side: RHS 184B (greyed purple group). Old foliage: Upper side: RHS 146A (yellow-green group). Lower side: RHS 137D (green group).

Leaflets:

*Size*.—About 6 cm long×4.2 cm wide.

*Shape*.—Round.

*Base shape*.—Obtuse.

*Apex shape*.—Acuminate.

*Texture*.—Leathery.

*Edge*.—Serrated.

*Serrations*.—Single.

*Petiole*.—Color: RHS 143C (green group) with RHS 184B (greyed-purple group). Length: 4 cm. Width: 2 mm. Surface Texture: Glandular with prickles on underside.

*Petiole rachis*.—Color: RHS 184B (greyed-purple group) with RHS 143C (green group). Underside: with prickles.

*Stipules*.—Length: 3 cm, smooth with glandular edges. Color: RHS 143C (green group).

*Auricle*.—Shape: Lanceolate. Length: 12 mm. Width: 2 mm. Color: RHS 143C (green group).

*Vein color*.—Color: Same as leaf color.

*Venation pattern*.—Reticulate.

Wood:

*New wood*.—Color: RHS 184B (greyed-purple group). Bark: Smooth.

*Old wood*.—Color: RHS 143C (green group). Bark: Smooth.

Branching habit:

*Number*.—4.

*Branching dimension*.—Length: 40 cm. Diameter: 5 mm.

Stems:

*Mature stem*.—Length: 60 cm. Diameter: 7 mm.

*Internode distance*.—6-7 cm. The above measurements are all variable, depending on growing conditions in a season.

*Stem pubescence present*.—No.

Prickles:

*Quantity*.—On main canes from base: Few. Number per stem length: 5 per 10 cm. On laterals from main canes: Few. Number per stem length: 3 per 10 cm.

*Form*.—Deep concave.

*Length*.—4 mm.

*Color when young*.—RHS 143C (green group).

*Color when mature*.—RHS 166C (greyed-orange group).

Small prickles:

*Quantity*.—Main stalk: None. Laterals: None.

Disease resistance:

*Powdery mildew*.—Resistant.

*Downy mildew*.—Resistant.

*Blackspot*.—Resistant.

*Rust*.—Resistant.

Pest resistance: Not tested.

Winter hardiness: Not tested.

Growing conditions: Normal garden conditions.

What is claimed is:

1. A new and distinct variety of rose plant of the shrub class, substantially as herein shown and described.

* * * * *

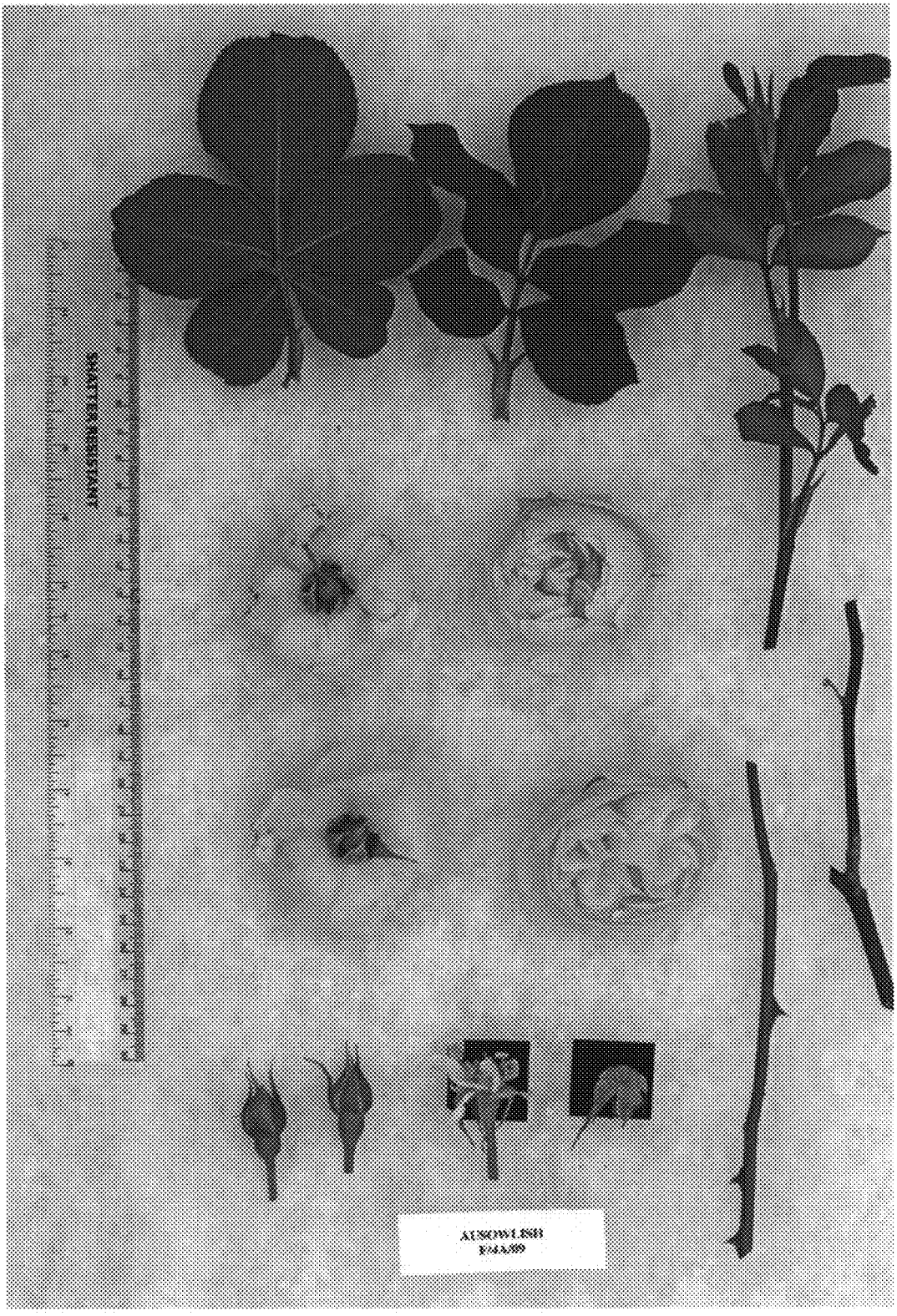
AUSOWLESB
F4A/99